(12) United States Patent
Zhu et al.

(10) Patent No.: US 12,171,862 B2
(45) Date of Patent: Dec. 24, 2024

(54) PERSONAL WASHING COMPOSITION AND METHOD OF ACHIEVING IMPROVED CONDITIONING BENEFITS

(71) Applicant: BASF SE, Ludwigshafen (DE)

(72) Inventors: Ben Chuan Zhu, Shanghai (CN); Lan Liao, Shanghai (CN); Zhen Yuan Qu, Shanghai (CN)

(73) Assignee: BASF SE (DE)

( * ) Notice: Subject to any disclaimer, the term of this patent is extended or adjusted under 35 U.S.C. 154(b) by 562 days.

(21) Appl. No.: 17/606,096

(22) PCT Filed: Apr. 28, 2020

(86) PCT No.: PCT/EP2020/061783
§ 371 (c)(1),
(2) Date: Oct. 25, 2021

(87) PCT Pub. No.: WO2020/225035
PCT Pub. Date: Nov. 12, 2020

(65) Prior Publication Data
US 2022/0192966 A1 Jun. 23, 2022

(30) Foreign Application Priority Data
May 9, 2019 (WO) ................ PCT/CN2019/086203

(51) Int. Cl.
| | |
|---|---|
| *C11D 1/00* | (2006.01) |
| *A61K 8/04* | (2006.01) |
| *A61K 8/40* | (2006.01) |
| *A61K 8/44* | (2006.01) |
| *A61K 8/46* | (2006.01) |
| *A61K 8/60* | (2006.01) |
| *A61K 8/73* | (2006.01) |
| *A61K 8/81* | (2006.01) |
| *A61Q 5/02* | (2006.01) |
| *A61Q 5/06* | (2006.01) |
| *A61Q 5/12* | (2006.01) |
| *A61Q 19/10* | (2006.01) |
| *C11D 1/02* | (2006.01) |
| *C11D 3/37* | (2006.01) |

(52) U.S. Cl.
CPC ............ *A61K 8/8158* (2013.01); *A61K 8/044* (2013.01); *A61K 8/44* (2013.01); *A61K 8/442* (2013.01); *A61K 8/466* (2013.01); *A61K 8/602* (2013.01); *A61K 8/731* (2013.01); *A61K 8/737* (2013.01); *A61K 8/8152* (2013.01); *A61Q 5/02* (2013.01); *A61Q 5/06* (2013.01); *A61Q 5/12* (2013.01); *A61Q 19/10* (2013.01); *A61K 2800/48* (2013.01); *A61K 2800/594* (2013.01); *A61K 2800/596* (2013.01)

(58) Field of Classification Search
CPC .......... C11D 1/00; C11D 1/02; C11D 3/3746; C11D 3/3757; C11D 3/3769; C11D 3/378; A61K 8/04; A61K 8/40; A61K 8/46; A61K 8/60; A61K 8/73; A61K 8/81; A61Q 5/02; A61Q 5/06; A61Q 5/12; A61Q 19/10
See application file for complete search history.

(56) References Cited

U.S. PATENT DOCUMENTS

| | | |
|---|---|---|
| 2,798,053 A | 7/1957 | Brown |
| 4,509,949 A | 4/1985 | Huang et al. |
| 5,087,445 A | 2/1992 | Haffey et al. |
| 5,288,814 A | 2/1994 | Long et al. |
| 7,455,848 B2 | 11/2008 | Hessefort et al. |
| 2012/0213725 A1 | 8/2012 | Galleguillos et al. |
| 2015/0335555 A1 | 11/2015 | Dobrowolski et al. |
| 2018/0311135 A1* | 11/2018 | Chang .................... A61K 8/731 |
| 2018/0311136 A1 | 11/2018 | Chang et al. |

FOREIGN PATENT DOCUMENTS

| | | |
|---|---|---|
| WO | WO-2008/129493 A2 | 10/2008 |
| WO | WO-2015/042020 A1 | 3/2015 |

OTHER PUBLICATIONS

International Application No. PCT/EP2020/061783, International Search Report and Written Opinion, mailed Jun. 29, 2020.

* cited by examiner

*Primary Examiner* — Brian P Mruk
(74) *Attorney, Agent, or Firm* — Faegre Drinker Biddle & Reath LLP

(57) ABSTRACT

The present invention relates to a personal washing composition comprising a detersive surfactant, at least one rheology modifying polymer, at least one cationic conditioning polymer, at least one benefit agent, and an anionic polymer of polysulfonic acid. The composition is a sulfate-free or substantial sulfate-free personal washing composition. The present invention further relates to a method of achieving improved conditioning benefits and/or improved deposition of benefit agents onto hair and/or skin.

19 Claims, No Drawings

PERSONAL WASHING COMPOSITION AND METHOD OF ACHIEVING IMPROVED CONDITIONING BENEFITS

CROSS-REFERENCE TO RELATED APPLICATIONS

This is the U.S. national phase of International Application No. PCT/EP2020/061783, filed Apr. 28, 2020, which claims the benefit of International Patent Application No. PCT/CN2019/086203, filed on May 9, 2019.

TECHNICAL FIELD

The present invention relates to a personal washing composition. The invention also relates to a sulfate-free personal washing composition, having improved deposition of conditioning benefit agents. More particularly, the invention relates to a method of achieving improved conditioning benefits by applying the composition onto the hair and/or skin.

BACKGROUND ART

Conventional personal washing compositions, such as shampoos, body washes and liquid hand soaps, contain standard surfactants such as anionic, nonionic and/or amphoteric type surfactants. Sulfate-based surfactant systems (such as, but not limited to, sodium lauryl sulfate and sodium lauryl ether sulfate) are typically employed because of their effectiveness in foam production and stability, and in deposition of conditioners/health aids to a target substrate such as hair or skin. Such deposition is believed to be via polymer-surfactant complexes, known as coacervates, which are formed upon dilution with water. The conditioners/health aids are entrapped by the coacervates which precipitate out of solution for deposition onto the substrate, thus delivering the conditioners/health aids. Personal washing compositions containing sulfate-based surfactants are generally easy to thicken with typical thickeners, such as salt and cellulose-based materials.

However, personal care compositions including sulfate-containing surfactants present also significant drawbacks. As a matter of fact, sulfate-containing surfactants such as sodium laureth sulfate (SLS) are known to be liable to give rise to tolerance problems, especially on the skin and the eyes. Another drawback of sulfate-containing surfactants is their tendency to strip the skin, scalp or hair of its natural oils, fats or proteins contained at their surface. In the long term the repeated use of personal care compositions including sulfate-containing surfactants may therefore cause irritation to the skin or scalp and/or give damage on hair fibers.

In addition, sulfate-free cleansing composition are difficult to thicken sufficiently to afford the user good usage qualities. Some attempts have been made in the prior art to thicken such formulas. U.S. patent 2015/0335555 disclosed one approach which was to use high levels of surfactants to benefit from the self-assembling properties of such ingredients. This approach is most common, but it is also costly. The second approach is to use rheology modifying polymer which can adversely impact the properties of the composition such as leading to poor deposition of conditioners/benefit agents from the composition. For example, the use of surfactant-polymer blends to increase the viscosity of cleansing compositions is described in U.S. patent 2012/0213725. However, as mentioned above, use of such rheology modifying polymer can adversely affect both the cleansing and/or foaming properties of cleansing composition requiring the use of increased amounts of the cleansing surfactants and cause negative impact on formation of coacervates and deposition of benefit agents.

In recent time, there is thus an increasing demand for personal care compositions including safe, environmentally friendly, and/or mild surfactants, and especially for sulfate-free personal care compositions.

It is thus an object of the present invention to address the ever-increasing demand in the market for personal care compositions, particularly a personal washing composition, more particularly a shampoo, which utilizes sulfate-free surfactants and provides enhanced deposition of conditioners/benefit agents from the composition.

SUMMARY OF THE INVENTION

In one aspect, the present invention is directed to a personal washing composition with enhanced deposition of benefit agents, said composition comprising:
  a) a detersive surfactant selected from the group consisting of anionic surfactants, amphoteric surfactants, zwitterionic surfactants, and combinations thereof,
  b) at least one rheology modifying polymer,
  c) at least one cationic conditioning polymer,
  d) at least one benefit agent in an effective amount to condition hair or skin,
  e) an anionic polymer of polysulfonic acid which comprises pendant sulfonate ($-SO_3^-$) and/or pendant sulfonic acid group ($-SO_3H$); preferably the polysulfonic acid comprises at least one monomer having ethylenic unsaturation with a sulfonic group,
  f) a cosmetically acceptable carrier;

In particular, the personal washing composition is preferred which is sulfate-free or substantially sulfate-free.

Preferably, the at least one rheology modifying polymer is an associative rheology modifying polymer, including hydrophobically modified alkali-swellable and alkali-soluble emulsion polymers, such as hydrophobically modified poly(meth)acrylates which are made by copolymerizing a mixture of (meth)acrylic monomers with hydrophobic co-monomer(s); hydrophobically modified ethylene oxide urethane polymers; hydrophobically modified polyethers; hydrophobically modified hydroxyethyl cellulose polymers, hydrophobically modified hydroxypropyl guar polymers or mixtures thereof.

Preferably, the at least one anionic polymer of polysulfonic acid comprising at least one monomer having ethylenic unsaturation with a sulfonic group, wherein the monomer is selected from the group consisting of 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, benzenesulfonic acid, toluene- or naphthalene-sulfonic acids, benzene- or naphthalenedisulfonic acids, alkylated benzene- or naphthalene-sulfonic acids, vinylsulfonic acid, 3-sulfopropyl acrylate, 3-sulfopropyl methacrylate, sulfomethacrylamide, sulfomethylmethacrylamide and mixtures thereof.

Preferably, the benefit agent is selected from insoluble or partially insoluble ingredients, such as moisturizers or conditioners, vitamins, vitamin derivatives, hair coloring agents, silica, pearlizer, anti-UV agents, anti-wrinkle agents, anti-aging agents, antiperspirants, deodorants, abrasives, fragrances or essential oils, skin-coloring agents, anti-microbial agents, anti-dandruff agents and/or mixtures thereof; more preferably, the benefit agent is anti-dandruff agent.

In a further aspect, the present invention relates to a method of achieving improved conditioning benefits, comprising applying to skin and/or hair the personal washing composition, in particular, the personal washing composition is sulfate-free or sulfate-substantial free.

In still a further aspect, the present invention relates to a method of achieving improved deposition of a hair and/or skin care benefit agent onto hair and/or skin, comprising applying to hair and/or skin the personal washing composition; in still a further aspect, the present invention relates to a method of achieving improved deposition of a hair and/or skin care benefit agents which are dispersed in the composition and have a small particle size, comprising applying to hair and/or skin the personal washing composition; in particular, the personal washing composition is sulfate-free or sulfate-substantial free.

In another aspect, the present invention relates to use of the personal washing composition caring for and washing keratinous materials, such as the hair and the skin.

It has been discovered that, the sulfate-free personal washing composition of the present invention, can bring about improved coacervate properties which result in enhanced conditioning and deposition of skin/hair actives, meanwhile, the composition also has desirable viscosity/rheological profile.

Without being limited to the theory, the sulfate-free personal washing composition of the present invention, is capable of not only providing a desired viscosity for use as personal care cleansing composition but also mitigate adverse effects caused by using rheology modifying polymer for thickening sulfate-free compositions. Without being limited to the theory, when the composition of the present invention contains benefit agents, the composition can provide further conditioning benefits due to sufficient deposition of conditioning agents. Without being limited to the theory, it is believed that; one preferred embodiment of the composition of the present invention is that containing benefit agents which are dispersed in the composition and have a smaller particle size, since such agents are believed to be absorbed or adhered to the surface of the coacervates, or be incorporated into the coacervates, and then effectively deposit on the skin/hair together with the coacervates.

DETAILED DESCRIPTION OF THE INVENTION

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art.

Further, unless otherwise required by context, singular terms shall include pluralities and plural terms shall include the singular.

All of the compositions and/or methods disclosed herein can be made and executed without undue experimentation in light of the present disclosure. While the compositions and methods of the presently disclosed and/or claimed inventive concept(s) have been described in terms of preferred embodiments, it will be apparent to those of ordinary skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the presently disclosed and/or claimed inventive concept(s).

As utilized in accordance with the present disclosure, the following terms, unless otherwise indicated, shall be understood to have the following meanings.

Throughout the description, including the claims, the term "comprising one" or "comprising a" should be understood as being synonymous with the term "comprising at least one", unless otherwise specified, and "between" should be understood as being inclusive of the limits.

The terms "a", "an" and "the" are used to refer to one or to more than one (i.e., to at least one) of the grammatical object of the article.

The term "and/or" includes the meanings "and", "or" and also all the other possible combinations of the elements connected to this term.

The term "substantially sulfate-free" in the context of the present invention is to be understood that the composition do not have significant amounts of sulfated compounds which exert a surfactant effect. In particular, here below to be understood that sulfated compounds in amounts of less than 0.01 wt. % are contained based on the total composition, in more particular, no detectable amounts.

The term "personal washing composition" as used herein refers to a composition of the present invention, wherein the composition is intended include those compositions for topical application to the hair or skin.

The term "benefit agent" as used herein should be broadly understood and intends an agent which when included in a personal washing composition in an appropriate amount is intended to produce a hair and/or skin care benefit.

The term "rheology modifying polymer" as used herein refers to a polymer deals with the property of the polymer to change the rheological properties of a given composition.

The term "polymer" as used herein refers to the product of a polymerization reaction, and is inclusive of homopolymers, copolymers, terpolymers, tetrapolymers, etc.; "copolymer" herein refers to a polymer formed by the polymerization reaction of at least two different monomers and is inclusive of random copolymers, block copolymers, graft copolymers, etc.

The term "derivative" as used herein, includes but is not limited to, amide, ether, ester, amino, carboxyl, acetyl, acid, salt and/or alcohol derivatives of a given compound.

The term "charge density" as used herein, means the ratio of the number of positive charges on a monomeric unit (of which a polymer is comprised) to the molecular weight of said monomeric unit. The charge density multiplied by the polymer molecular weight determines the number of positively charged sites on a given polymer chain.

The term "coacervate" used herein refers to the chemical complex formed between cationic polymer and anionic surfactant/polymer upon dilution of the personal washing composition. "Coacervate" without being limited to a particular theory, provide improved hair and skin conditioning without any additional conditioning actives. Further, when dispersed conditioning agent droplets are added to the matrix, the coacervate provides an improved mechanism for conditioning agent deposition, yielding conditioning agent deposition that results in even more of a conditioning benefit.

The term "cosmetically acceptable" refers to ingredients typically used in personal care compositions and is intended to underscore that materials that are toxic when present in the amounts typically found in personal care compositions are not contemplated as part of the present invention.

In one aspect, the present invention is directed to a personal washing composition with enhanced deposition of benefit agents, said composition comprising:
 a) a detersive surfactant selected from the group consisting of anionic surfactants, amphoteric surfactants, zwitterionic surfactants, and combinations thereof,
 b) at least one rheology modifying polymer,
 c) at least one cationic conditioning polymer,
 d) at least one benefit agent in an effective amount to condition hair or skin,
 e) an anionic polymer of polysulfonic acid which comprises pendant sulfonate ($-SO_3^-$) and/or pendant sulfonic acid group ($-SO_3H$); preferably the polysulfonic acid comprises at least one monomer having ethylenic unsaturation with a sulfonic group,
 f) a cosmetically acceptable carrier;

In particular, the personal washing composition is preferred which is sulfate-free or substantially sulfate-free.

Detersive Surfactant

The personal washing composition of the present invention comprises a detersive surfactant selected from the group consisting of anionic surfactants, amphoteric surfactants, zwitterionic surfactants, and combination thereof. In particular, the surfactants used in the present invention are sulfate-free surfactants or substantially sulfate-free surfactants.

Suitable anionic surfactants used in the present invention, either alone or as part of the nonionic/anionic surfactant mixture, include substances having a negatively charged hydrophobe or that carry a negative charge when the pH is elevated to neutrality or above, such as acylamino acids, and salts thereof, for example, acylglutamates, acyl peptides, sarcosinates, and taurates; carboxylic acids, and salts thereof, for example, alkanolic acids and alkanoates, ester carboxylic acids, and ether carboxylic acids; phosphoric acid ester and salts thereof; sulfonic acids and salts thereof, for example, acyl isethionates, alkylaryl sulfonates, alkyl sulfonates, and sulfosuccinates. Non-limiting examples of anionic surfactants, used either alone or as part of the nonionic/anionic surfactant mixture, include mono-basic salts of acylglutamates that are slightly acidic in aqueous solution, such as sodium acylglutamate and sodium hydrogenated tallow glutamate; salts of acyl-hydrolyzed protein, such as potassium, palmitoyl hydrolyzed milk protein, sodium cocoyl hydrolyzed soy protein, and TEA-abietoyl hydrolyzed collagen; salts of acyl sarcosinates, such as ammonium myristoyl sarcosine, sodium cocoyl sarcosinate, and TEA-lauroyl sarcosinate; salts of sodium methyl acyltaurates, such as sodium lauroyl taurate and sodium methyl cocoyl taurate; alkanoic acids and alkanoates, such as fatty acids derived from animal and vegetable glycerides that form water-soluble soaps and water-insoluble emulsifying soaps, including sodium stearate, aluminum stearate, and zinc undecylenate; ester carboxylic acids, such as dinonoxynol-9-citrate; salts of acyl lactylates such as calcium stearoyl lactylate and laureth-6 citrate; ethercarboxylic acids derived from ethoxylated alcohols or phenols having varying lengths of polyoxyethylene chains, such as nonoxynol-8 carboxylic acid, and sodium trideceth-13 carboxylate; mono- and di-esters of phosphoric acid and their salts, such as phospholipids, dilaureth-4-phosphate, DEA-oleth-10 phosphate and triethanolamine lauryl phosphate; salts of acylisethionate, such as sodium cocoyl isethionate; alkylarylbenzene sulfonates, such as alpha-olefin sulfonate and alkali metal, alkaline earth metal, and alkanolamine salts thereof, and sodium dodecylbenzene sulfonate; alkyl sulfonates, such as sodium $C_{12}$-$C_{14}$ olefin sulfonate, sodium cocomonoglyceride sulfonate, sodium $C_{12}$-$C_{15}$ pareth-15 sulfonate, and sodium lauryl sulfoacetate; sulfosuccinates, such as mono- and di-esters of sulfosuccinic acid, salts thereof and alkoxylated alkyl and alkylamido derivatives thereof, such as di-$C_4$-$C_{12}$ alkyl sodium sulfosuccinate, disodium laureth sulfosuccinate, disodium oleamido MEA-sulfosuccinate, and disodium $C_{12}$-$C_{15}$ pareth sulfosuccinate, and the like.

In some preferred embodiments, the anionic surfactant, used either alone or as part of the nonionic/anionic surfactant mixture, can comprise, consist of, or consist essentially of a compound selected from the group consisting of an ammonium, alkali or earth alkali salt of: a sulfonate, a sulfosuccinate, a carboxylate, a sarcosinate, an isethionate, a sulfoacetate; and combinations thereof. More particularly, the anionic surfactant, used either alone or as part of the nonionic/anionic surfactant mixture, can comprise, consist of, or consist essentially of a compound selected from the group consisting of sodium alpha-olefin sulfonate, disodium laureth sulfosuccinate, sodium laureth-5 (13) carboxylate, sodium lauroyl sarcosinate, sodium cocoyl isethionate, sodium lauryl sulfoacetate, and combinations thereof.

Amphoteric surfactants used in the present invention, can comprise, consist of, or consist essentially of a compound selected from the group consisting of coco amido propyl betaine, cocoamido hydroxyl sultaine, cocoamphoacetate, sodium methyl cocoyl taurate, and combinations thereof.

Nonionic surfactants used in the present invention, can comprise, consist of, or consist essentially of a compound selected from the group consisting of an alkyl glucoside, cocoamide monoethanolamine, cocoamide diethanolamine, a glycerol alkyl ester, polyethylene glycol, and combinations thereof.

Suitable anionic surfactant components for use in the personal washing composition herein include those that are known for use in hair care or other personal care compositions. The concentration of the anionic surfactant system in the personal washing composition should be sufficient to provide the desired cleaning and lather performance, and generally ranges from about 5 wt % to about 50 wt %, preferably from about 8 wt % to about 30 wt %, more preferably from about 10 wt % to about 25 wt %, based on the total weight of the composition.

Rheology Modifying Polymer

Rheology modifying polymers are used to control the viscosity of a variety of consumer and commercial products, including personal cleansing composition, such as shampoo and body wash. The rheology modifying polymer may be used to thicken a formulation to provide a more appealing viscosity and to provide desirable flow characteristics, and can also be used to suspend encapsulated additives, solid particles or gas bubbles within a formulation for extended period of time, effectively preventing settling.

Suitable rheology modifying polymer for the present invention include synthetic and semi-synthetic rheology modifying polymer. Exemplary synthetic rheology modifying polymer include acrylic based polymers and copolymers. One class of acrylic based rheology modifying polymers are the carboxyl functional alkali-swellable and alkali-soluble thickeners produced by the free-radical polymerization of acrylic acid alone or in combination with other ethylenically unsaturated monomers. The polymers can be synthesized by solvent/precipitation as well as emulsion polymerization techniques. Exemplary synthetic rheology modifying polymer of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule wherein the substituent is preferably and independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. Nos. 5,087,445; 4,509,949; and 2,798,053 herein incorporated by reference in its entirety.

In a further aspect the rheology modifying polymer is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814.

In some embodiments of the present invention, another class of synthetic rheology modifying polymer suitable for use in accordance with an embodiment of the present invention includes hydrophobically modified alkali-swellable and alkali-soluble emulsion polymers. Typical hydrophobically modified alkali-swellable polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), and an optional "associative monomer" and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

In some embodiments of the present invention, another class of synthetic and semi-synthetic rheology modifying polymers suitable for use in accordance with an embodiment of the present invention includes cationically modified acrylic polymers and copolymers and cationically modified cellulose ethers. The acrylic polymers and copolymers and cellulose ethers are cationically modified via quaternization. For the acrylic polymers and copolymers, quaternization can occur by polymerizing a quaternized monomer into the acrylic polymer backbone or by post functionalizing the acrylic polymer with a quaternizing agent.

More preferably, the rheology modifying polymer used in the present invention is an associative rheology modifying polymer, which means an amphiphilic polymer that is capable, in an aqueous medium, of reversible combining with itself or with other molecules. It generally comprises in its chemical structure at least one hydrophilic zone or group and at least one hydrophobic zone or group. Suitable examples include: i) celluloses modified with groups comprising at least one fatty chain (hydrophobically modified cellulose), such as hydroxyethylcelluloses modified with groups comprising at least one fatty chain, such as alkyl, arylalkyl or alkylacryl groups or a mixture thereof, and in which the alkyl groups are preferably $C_8$-$C_{22}$ (hydrophobically modified hydroxyethylcellulose polymers); and/or cellulose modified with polyalkylene glycol alkylphenyl ether groups, such as the product Amercell Polymer-HM-1500 (nonylphenyl polyethylene glycol (15) ether) sold by the company Amerchol; ii) hydroxypropyl guars modified with groups comprising at least one $C_8$-$C_{30}$ fatty chain (hydrophobically modified hydropropyl guar polymers), such as the product RE210-18 ($C_{14}$ alkyl chain) sold by the company Rhodia; iii) hydrophobically modified polyethers; iv) hydrophobically modified ethylene oxide urethane polymers; v) hydrophobically modified alkali-soluble or swellable emulsion polymers, such as hydrophobically modified poly (meth)acrylates which are made by copolymerizing a mixture of (meth)acrylic monomers with hydrophobic co-monomer(s). Suitable rheology modifying polymers useful for the present invention are commercially available, for example, Rheocare® TTA (2-methyl-2-propenoic acid polymer with butyl 2-propenoate and ethyl 2-propenoate), Salcare® SC 81, Luvigel® FIT, Salcare® SC 80 and Tinovis® GTC from BASF.

According to any one of the invention embodiments, the rheology modifying polymer is present in the personal washing composition in an amount sufficient to impart the desired rheology profile to the desired composition. In particular, when the composition comprises insoluble or partially insoluble ingredients, the rheology modifying agent is used in an amount sufficient to suspend encapsulated additives, solid particles or gas bubbles and to effectively prevent settling. By way of non-limiting example, the amount of rheology modifying polymer is present in an amount ranging from 0.05 wt to 10 wt %, for example from 0.1 wt to 5 wt %, for example, from 0.1 wt to 3 wt %, based on the total weight of the composition.

Anionic Polymer of Polysulfonic Acid

According to any one of the invention embodiments, the personal washing composition comprises at least one anionic polymer of polysulfonic acid which comprise pendant sulfonate ($-SO_3^-$) and/or pendant sulfonic acid group ($-SO_3H$).

In some embodiments, the personal washing composition comprises at least one anionic polymer of polysulfonic acid comprising at least one monomer having ethylenic unsaturation with a sulfonic group. The anionic polymer can be homopolymeric and/or copolymeric polysulfonic acid. Preferred monomers containing sulfonic acid groups are those of the formula $R^1(R^2)C=C(R^3)-X-SO_3H$, in which $R^1$ to $R^3$ mutually independently denote $-H$, $-CH_3$, a straight-chain or branched saturated alkyl residue with 2 to 12 carbon atoms, a straight-chain or branched, mono- or polyunsaturated alkenyl residue with 2 to 12 carbon atoms, alkyl or alkenyl residues substituted with $-NH_2$, $-OH$ or $-COOH$, or denote $-COOH$ or $-COOR^4$, wherein $R^4$ is a saturated or unsaturated, straight-chain or branched hydrocarbon residue with 1 to 12 carbon atoms, and X denotes an optionally present spacer group which is selected from $-(CH_2)n-$ with n being an integer of 0 to 4, $-COO-(CH_2)_m$ with m being an integer of 1 to 6, $-C(O)-NH-C(CH_3)_2-$, $-C(O)-NH-C(CH_3)_2CH_2-$ and $-C(O)-NH-CH(CH_3)-CH_2-$.

Preferred among these monomers are those of the formulae below:

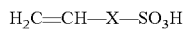

$H_2C=CH-X-SO_3H$

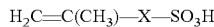

$H_2C=C(CH_3)-X-SO_3H$

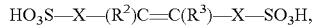

$HO_3S-X-(R^2)C=C(R^3)-X-SO_3H$, in which $R^2$ and $R^3$ are mutually independently selected from $-H$, $-CH_3$, $-CH_2CH_3$, $-CH_2CH_2CH_3$, $-CH(CH_3)_2$ and X denotes an optionally present spacer group, which is selected from $-(CH_2)_n-$ with n being an integer of 0 to 4, $-COO-(CH_2)_m-$ with m being an integer of 1 to 6, $-C(O)-NH-C(CH_3)_2-$, $-C(O)-NH-C(CH_3)_2-CH_2-$ and $-C(O)-NH-CH(CH_3)-CH_2-$.

In some embodiments, more preferred monomers containing sulfonic acid groups are here 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propene-1-sulfonic acid, styrenesulfonic acid, benzenesulfonic acid, toluene- or naphthalene-sulfonic acids, benzene- or naphthalenedisulfonic acids, alkylated benzene- or naphthalene-sulfonic acids, vinylsulfonic acid, 3-sulfopropyl acrylate, 3-sulfopropyl methacrylate, sulfomethacrylamide, sulfomethylmethacrylamide and mixtures of the stated acids or the water-soluble salts thereof. Preferably, suitable polysulfonic acids for the present invention include homopolymer of acrylamido-2-methylpropanesulfonate, copolymer of acrylamido-2-methylpropanesulfonate or a combination thereof.

In some embodiments, the polysulfonic acids suitable for the present invention are the natural polymers, including, but not being limited to lignosulfonate, alkylsuccynyl soy sulfonate such as sodium $C_8-C_{16}$ isoalkylsuccinyl soy sulfonate, alkylsuccinyl lactoglobulin sulfonate such as sodium $C_8-C_{16}$ isoalkylsuccinyl lactoglobulin sulfonate, shale oil sulfonate, hydeoxyethylcellulose sulfonate such as sodium stearoxy PG-hydroxyethylcellulose sulfonate, guaiazulene sulfonate, and alkylglucoside sulfonate such as hydroxypropylsulfonate laurylglucoside crosspolymer.

The sulfonic acid groups may be present in the polymers entirely or in part in neutralized form, i.e. the acidic hydrogen atom of the sulfonic acid group may be replaced in some or all of the sulfonic acid groups with metal ions, preferably alkali metal ions and in particular with sodium ions. It is preferred according to the invention to use copolymers containing partially or completely neutralized sulfonic acid groups.

In some embodiments, the anionic polymer can be copolymeric polysulfonic acid, which contain monomers containing carboxylic acid groups and monomers containing sulfonic acid groups. In some preferred embodiments, the copolymer comprises from 5 to 95 wt. %, preferably from 20 to 90 wt. %, more preferably from 40 to 60 wt. % the monomer containing sulfonic acid, based on the total weight of the copolymer.

Suitable unsaturated carboxylic acid(s) monomer for the present invention, is unsaturated carboxylic acids of the formula $R^5(R^6)C=C(R^7)COOH$, in which $R^5$ to $R^7$ mutually independently denote $-H$, $-CH_3$, a straight-chain or branched saturated alkyl residue with 2 to 12 carbon atoms, a straight-chain or branched, mono- or polyunsaturated alkenyl residue with 2 to 12 carbon atoms, alkyl or alkenyl residues substituted with $-NH_2$, $-OH$ or $-COOH$ as defined above or denote $-COOH$ or $-COOR^8$, wherein $R^8$ is a saturated or unsaturated, straight-chain or branched hydrocarbon residue with 1 to 12 carbon atoms.

In some embodiments, the copolymer comprises 5 wt % to 95 wt %, preferably from 10 wt % to 80 wt %, more preferably from 40 wt % to 60 wt % the monomer containing carboxylic acid groups, based on the total weight of the copolymer. More preferred unsaturated carboxylic acids are acrylic acid, methacrylic acid, ethacrylic acid, α-chloroacrylic acid, α-cyanoacrylic acid, crotonic acid, α-phenylacrylic acid, maleic acid, maleic anhydride, fumaric acid, itaconic acid, citraconic acid, methylenemalonic acid, sorbic acid, cinnamic acid or mixtures thereof. Unsaturated dicarboxylic acids may also be used. In some embodiments, in addition to a monomer containing carboxyl groups and a monomer containing sulfonic acid groups, the copolymers may optionally further comprise at least one nonionic monomer.

According to any one of the invention embodiments, the charge density and average molar mass (Mw) of the anionic polymer of polysulfonic acid may be varied in order to tailor the properties of the polymers to the desired intended application. In some preferred embodiments for being used in personal washing composition, the polymers exhibit a charge density from 0.1 meq/g to 9.5 meq/g, preferably from 0.5 meq/g to 7.0 meq/g, more preferably from 1.0 meq/g to 6.5 meq/g, still more preferably from 1.5 meq/g to 5.5 meq/g and the polymers exhibit average molar masses (Mw) of 1,000 to 2,000,000 g/mol, preferably of 10,000-2,000,000 g/mol.

According to any one of the invention embodiments, the anionic polymer of polysulfonic acid is present in the personal washing composition in an effective amount to coacervate with an oppositely-charged compound. The polysulfonic acid will typically be present a level of from 0.01 wt % to 10 wt %, preferably from 0.05 wt % to 5 wt %, more preferably from 0.1 wt % to 2 wt %, still more preferably from 0.1 wt % to 1 wt %, based on the total weight of the composition.

Cationic Conditioning Polymer

The personal washing composition of the present invention comprises a cationic conditioning polymer for enhancing conditioning performance of the composition. The cationic conditioning polymer may be a homopolymer or be formed from two or more types of monomers. The molecular weight of the polymer will generally be between 5,000 and 10,000,000 g/mol, typically at least 10,000 g/mol and preferably in the range of from 100,000 to about 2,000,000 g/mol. The polymers will have cationic nitrogen containing groups such as quaternary ammonium or protonated amino groups, or a mixture thereof. The cationic nitrogen-containing group will generally be present as a substituent on a fraction of the total monomer units of the cationic polymer. Thus, when the polymer is not a homopolymer it can contain spacer non-cationic monomer units. Such polymers are described in the CTFA Cosmetic Ingredient Directory, $3^{rd}$ edition. The ratio of the cationic to non-cationic monomer units is selected to give a polymer having a cationic charge density in the required range.

Suitable cationic conditioning polymers include, for example, copolymers of cationic vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general, secondary and tertiary amines, especially tertiary, are preferred. Amine substituted vinyl monomers and amines can be polymerized in the amine form and then converted to ammonium by quaternization. The cationic conditioning polymers can comprise mixtures of monomer units derived from amine- and/or quaternary ammonium-substituted monomer and/or compatible spacer monomers. Suitable examples the synthetic cationic conditioning polymer of the present invention include, homopolymers and copolymers of dimethyl diallyl ammonium chloride (DMDAAC), homopolymers and copolymers of methacrylamidopropyl trimethyl ammonium chloride (MAPTAC), homopolymers and copolymers of acrylamidopropyl trimethyl ammonium chloride (APTAC), homopolymers and copolymers of methacryloyloxyethyl trimethyl ammonium chloride (METAC), homopolymers and copolymers of acryloyloxyethyl trimethyl ammonium chloride (AETAC), homopolymers and copolymers of methacryloyloxyethyl trimethyl ammonium methyl sulfate (METAMS).

Other suitable cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

According to any one of the invention embodiments, one of suitable cationic conditioning polymers can be cationic guar polymer, which is cationally substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of □(1-4) glycosidic linkages. The galactose branching arises by way of an □(1-6) linkage. Cationic derivatives of the guar gums are obtained by reaction between the hydroxyl groups of the polygalactomannan and reactive quaternary ammonium compounds. The cationic guar polymer has a weight average molecular weight of 10,000 to 5,000,000 g/mol, and has a charge density of from about 0.05 to about 2.5 meq/g; preferably, the cationic guar polymer has a weight average molecular weight of 15,000 to 2,500,000 g/mol, more preferably, of 200,000 to 1,500,000 g/mol; and has a charge density of from 0.2 to 2.2 meq/g, or 0.3 to 2.0 meq/g, or from 0.4 to 1.8 meq/g. Suitable cationic guar polymers include cationic guar gum derivatives, such as guar hydroxypropyltrimonium chloride. In some embodiments, the cationic guar polymer is a guar hydroxypropyltrimonium chloride. Specific examples of guar hydroxypropyltrimonium chlorides include the Jaguar® series commercially available from Rhone-Poulenc Incorporated. Other suitable guar hydroxypropyltrimonium chloride are: Hi-Care 1000, which has a charge density of about 0.7 meq/g and a molecular weight of 600,000 g/mol and is available from Rhodia, N-Hance 3269 and N-Hance 3270, which has a charge density of about 0.7 meq/g and a molecular weight of about 425,000 g/mol and is available from ASI. AquaCat CG518 has a charge density of 0.9 meq/g and a molecular weight of 50,000 g/mol and is available from ASI.

According to any one of the invention embodiments, one of suitable cationic conditioning polymer can be watersoluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cationically modified starch polymers for use in the personal washing compositions of the present invention have a molecular weight from about 850,000 to about 15,000,000 and/or from about 900,000 to about 5,000,000. The cationically modified starch polymers used in the present invention have a charge density of from 0.2 about meq/g to about 5 meq/g, preferably from about 0.2 meq/g to about 2 meq/g.

One of suitable types of cationic polysaccharides of the present invention is cationic cellulose, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67.

The cationic conditioning polymer will generally be present in compositions of the invention at levels of from 0.01 wt % to 10 wt %, preferably from 0.05% wt to 5 wt %, more preferably from 0.1 wt % to 2 wt % based on the total weight of the composition.

Benefit Agent

The personal washing compositions of the present invention comprise one or more benefit agents that can provide a positive and/or beneficial effect to the substrate being cleaned, e.g. to the hair and skin. The skilled person is able to select according to general knowledge in the art of formulating personal care compositions such as shampoos, shower gels and liquid hand soaps, and the vast literature there-related, appropriate such optional ingredients for application purposes. In one embodiment, the composition of the present invention further comprises one or more benefit agents, such as emollients, moisturizers, conditioners, skin conditioners, or hair conditioners such as silicones such as volatile silicones, gums or oils, or non-amino silicones and mixtures thereof, mineral oils, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, including acetylated lanolin alcohols, lanolin, lard, mink oil and tallow, and fatty acids and alcohols, including behenic acid, palmitic acid, stearic acid, behenyl alcohol, cetyl alcohol, eicosanyl alcohol and isocetyl alcohol; vitamins or their derivatives, such as vitamin B complex, including thiamine, nicotinic acid, biotin, pantothenic acid, choline, riboflavin, vitamin B6, vitamin B12, pyridoxine, inositol, carnitine, vitamins A,C,D,E,K and their derivatives, such as vitamin A palmitate, and pro-vitamins, e.g., panthenol (pro vitamin B5), panthenol triacetate and mixtures thereof; antioxidants; free-radical scavengers; abrasives, natural or synthetic; dyes; hair coloring agents; bleaching agents; hair bleaching agents; UV absorbers, such as benzophenone, bornelone, PABA (Para Amino Benzoic Acid), butyl PABA, cinnamidopropyl trimethyl ammonium chloride, disodium distyrylbiphenyl disulfonate, potassium methoxycinnamate; anti-UV agents, such as butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate 0), red petrolatum; antimicrobial agents; antibacterial agents, such as bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide; antifungal agents; melanin regulators; tanning accelerators; depigmenting agents, such as retinoids such as retinol, kojic acid and its derivatives such as, for example, kojic dipalmitate, hydroquinone and its derivatives such as arbutin, transexamic acid, vitamins such as niacin, vitamin C and its derivatives, azelaic acid, placertia, licorice, extracts such as chamomile and green tea, where retinol, kojic acid, and hydroquinone are preferred; skin lightening agents such as hydroquinone, catechol and its derivatives, ascorbic acid and its derivatives; skin coloring agents, such as dihydroxyacetone; liporegulators; weight-reduction agents; anti-acne agents; anti-seborrhoeic agents; anti-ageing agents; anti-wrinkle agents; keratolytic agents; anti-inflammatory agents; anti-acne agents, such as tretinoin, isotretinoin, motretinide, adapalene, tazarotene, azelaic acid, retinol, salicylic acid, benzoyl peroxide, resorcinol, antibiotics such as tetracycline and isomers thereof, erythromycin, anti-inflammatory agents such as ibuprofen, naproxen, hetprofen, botanical extracts such as *Alnus, Arnica, Artemisia capillaris, Asiasarum* root, calendula, chamomile, nidium, comfrey, fennel, galla rhois, hawthorn, *Houttuynia, Hypericum*, jujube, kiwi, licorice, *Magnolia*, olive, peppermint, philodendron, *Salvia, Sasa albomarginata*, imidazoles such as ketoconazole and elubiol; refreshing agents; cicatrizing agents; vascular-protection agents; agents for the reduction of dandruff (Anti-dandruff agent), seborrheic dermatitis, or psoriasis, such as pyrithione salts, being formed from heavy metals such as zinc, tin, cadmium, magnesium aluminum, sodium and zirconium, like zinc pyrithione, shale oil and derivatives thereof such as sulfonated shale oil, selenium sulfide, sulfur, salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone oleamine (Octopirox), selenium sulfide, ciclopirox oleamine, anti-psoriasis agents such as vitamin D analogs, e.g. calcipotriol, calcitriol, and tacaleitrol, vitamin A analogs such as esters of vitamin A, including vitamin A palmitate, retinoids, retinols, and retinoic acid, corticosteroids such as hydrocortisone, clobetasone, butyrate, clobetasol propionate; antiperspirants or deodorants, such as aluminum chlorohydrates, aluminum zirconium chlorohydrates; immunomodulators; nourishing agents; depilating agents, such as calcium thioglycolate, magnesium thioglycolate, potassium thioglycolate, strontium thioglycolate; agents for combating hair loss; reducing agents for permanent-waving; reflectants, such as mica, alumina, calcium silicate, glycol dioleate, glycol distearate, silica, sodium magnesium fluorosilicate; essential oils and fragrances.

In some embodiments, the present invention particularly provides a personal washing composition having an enhanced deposition of the benefit agents. The benefit agents are selected from insoluble or partially insoluble ingredients, such as moisturizers or conditioners, vitamins, vitamin derivatives, hair coloring agents, silica, pearlizer, anti-UV agents, anti-wrinkle agents, anti-aging agents, antiperspirants, deodorants, abrasives, fragrances or essential oils, skin-coloring agents, anti-microbial agents, anti-dandruff agents, onto the substrate, ex. hair and/or skin. In still some embodiments, the present invention more particularly provides a personal washing composition having an enhanced deposition of the benefit agents which are dispersed in the composition and have a small particle size. The benefit agents of small particles used in the personal washing composition typically have an average particle diameter ranging from about 0.01 μm to about of 400 μm, preferably from about 0.01 μm to about 200 μm, more preferably in the range of from about 0.01 μm to about 100 μm, and still more preferably in the range of from about 0.01 μm to about 50 μm, still further more preferably in the range of from about 0.01 μm to about 25 μm. One example of the present invention comprises anti-dandruff agents, which may be an anti-dandruff active particulate. In some embodiments, the anti-dandruff agent is selected from the group consisting of pyridinethione salts; zinc carbonate; azoles, such as ketoconazole, econazole, and elubiol; selenium sulphide; particulate sulfur; keratolytic agents such as salicylic acid; and mixtures thereof. In one embodiment, the anti-dandruff agent is a pyridinethione salt.

According to any one of the invention embodiments, the personal washing composition comprises from about 0.05 wt % to 80 wt %, preferably from 0.1 wt % to 40 wt %, and more preferably from 0.5 wt % to 20 wt % of benefit agents, based on the total weight of the composition.

According to any one of the invention embodiments, the personal washing composition further comprises a carrier, or a mixture of such carriers, which are suitable for application to the skin and/or hair. Suitable carriers for use with skin and/or hair washing compositions include water, $C_1$-$C_6$ alcohols, lower alkyl acetate and mixtures thereof. In some embodiments, the carriers can also contain a wide variety of additional materials such as acetone, hydrocarbons such as isobutane, hexane, decene, halogenated hydrocarbons and volatile silicones such as cyclomethicone. The carriers are present in the present personal washing composition ranging from about 0.5 wt % to about 99 wt %, preferably from about 5 wt % to about 99 wt %, more preferably from about 10 wt % to about 98 wt %, based on the total weight of the composition.

In some preferred embodiments of the present invention, the composition comprises:
a) a detersive surfactant selected from the group consisting of anionic surfactants, amphoteric surfactants, zwitterionic surfactants, and combinations thereof,
b) at least one rheology modifying polymer which is an associative rheology modifying polymer selected from the group consisting of hydrophobically modified alkali-swellable and alkali-soluble emulsion polymers; hydrophobically modified ethylene oxide urethane polymers; hydrophobically modified polyethers; hydrophobically modified hydroxyethyl cellulose polymers, hydrophobically modified hydroxypropyl guar polymers and mixtures thereof; preferably, the associative rheology modifying polymer is hydrophobically modified alkali-swellable and alkali-soluble emulsion polymer; more preferable, the hydrophobically modified alkali-swellable and alkali-soluble emulsion polymer is hydrophobically modified poly(meth)acrylates which are made by copolymerizing a mixture of (meth)acrylic monomers with hydrophobic co-monomer(s),
c) at least one cationic conditioning polymer selected from the group consisting of cationic polysaccharides and polymers comprising cationic vinyl monomers, such as cationic guar gum derivatives, cationic cellulose derivatives, cationic starch derivatives, homopolymers and copolymers of dimethyl diallyl ammonium chloride (DMDAAC), homopolymers and copolymers of methacrylamidopropyl trimethyl ammonium chloride (MAPTAC), homopolymers and copolymers of acrylamidopropyl trimethyl ammonium chloride (APTAC), homopolymers and copolymers of methacryloyloxyethyl trimethyl ammonium chloride (METAC), homopolymers and copolymers of acryloyloxyethyl trimethyl ammonium chloride (AETAC), homopolymers, copolymers of methacryloyloxyethyl trimethyl ammonium methyl sulfate (METAMS) and a combination thereof; Preferably, the cationic conditioning polymer is cationic guar gum derivatives, cationic cellulose derivatives or cationic starch derivatives;
d) at least one benefit agent in an effective amount to condition hair or skin, wherein the benefit agent is selected from insoluble or partially insoluble ingredients, such as moisturizers or conditioners, vitamins, vitamin derivatives, hair coloring agents, silica, pearlizer, anti-UV agents, anti-wrinkle agents, anti-aging agents, antiperspirants, deodorants, abrasives, fragrances or essential oils, skin-coloring agents, antimicrobials and anti-dandruff agents; preferably, the benefit agent has small particles dispersed in the composition; more preferably, the benefit agent is anti-dandruff agent; still more preferably, the anti-dandruff agent is selected from the group consisting of pyridinethione salts; zinc carbonate; azoles, such as ketoconazole, econazole, and elubiol; selenium sulphide; particulate sulfur; keratolytic agents such as salicylic acid; and mixtures thereof;
e) an anionic polymer of polysulfonic acid comprising at least one monomer having ethylenic unsaturation with a sulfonic group, wherein the monomer is selected from the group consisting of 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, benzenesulfonic acid, toluene- or naphthalenesulfonic acids, benzene- or naphthalenedisulfonic acids, alkylated benzene- or naphthalene-sulfonic acids, vinylsulfonic acid, 3-sulfopropyl acrylate, 3-sulfopropyl methacrylate, sulfomethacrylamide, sulfomethylmethacrylamide and mixtures thereof; preferably, the polysulfonic acid is homopolymer of acrylamido-2-methylpropanesulfonate, copolymer of acrylamido-2-methylpropanesulfonate;
f) a cosmetically acceptable carrier;

In particular, the composition is preferred which is sulfate-free or substantially sulfate-free.

According to any one of the invention embodiments, the personal washing composition is used in a manner know in the art, for example, in the case of a cleanser or shampoo, by application of the cleanser or shampoo to the skin and/or hair and optionally rinsing the cleanser or shampoo off of the skin and/or hair with water. The personal washing composition of the present invention may have a pH comprised between 4 and 11, for instance between 4 and 6.

The personal washing composition of the present invention can be prepared by mixing individual components using any conventional blending technique known in the prior art such as conventional stirring, shaking or tumbling. These components may be supplied as concentrated solutions which are diluted and/or and combined in appropriate ratios by the skilled person. The invention covers any concentrate to be used as component ingredient to prepare a composition of the invention, and especially to concentrates containing limited levels of water due to some reasons from a cost and environmental perspective.

In a further aspect, the present invention relates to a method of achieving improved conditioning benefits, comprising applying to skin and/or hair the personal washing composition.

In still a further aspect, the present invention relates to a method of achieving improved deposition of a hair and/or skin care benefit agent onto hair and/or skin, comprising applying to hair and/or skin the personal washing composition. In still a further aspect, the present invention relates to a method of achieving improved deposition of a hair and/or skin care benefit agents which are dispersed in the composition and have a small particle size, comprising applying to hair and/or skin the personal washing composition. Particularly, the personal washing composition is sulfate-free or sulfate-substantial free composition.

In another aspect, the present invention relates to use of the personal washing composition caring for and washing keratinous materials, such as the hair and the skin.

EXAMPLES

It is understood that the present invention is not limited to the embodiments specifically disclosed and exemplified herein. Various modifications of the invention will be apparent to those skilled in the art. Such changes and modifications may be made without departing from the scope of the appended claims.

The invention will now be described in further detail by way of the following non-limiting examples, wherein the abbreviations have the usual meaning in the art. The temperature are indicated in degree centigrade (° C.) and the other parameters in the respective current units. Water amount indicated as "q.s" are intended to be "the amount required to complete to 100%.
Evaluation Methodologies
Molecular Weight Measurement The average molecular weight (Mw) of polymers was determined by gel permeation chromatography (GPC) using TSKgel GMPWXL 13 μm*2, 300×7.8 mm columns and aqueous solution containing 0.01 M phosphate buffer and 0.1 M NaCl as eluent. The concentration of polymer is determined by refractive index detector and the molecular weight is calibrated with Poly(acrylic acid)-Na Salt standards.
Coacervate Weight Measurement The coacervate weight was measured using the coacervate centrifugation test. In this test the hair washing composition was diluted 1:9 with tap water. The diluted composition was mixed slowly for at least 2 hours and then centrifuged at 3500 rpm for 20 minutes. The supernate phase (top phase) was then removed and the weight of the coacervate phase (bottom phase) was measured (25° C., 50% RH).
Combing Force Measurement The physical measurement of combing forces on hair strands enable objectively measured results on how products like hair shampoos or hair conditioners perform with regards to conditioning and detangling efficacies. In a pre-post design, the reduction of wet or dry combing forces is determined to substantiate the efficacy.

Prior to measurement, the hair strand is detangled until no loops or coils remain. Next, the strand is positioned into a clamp and combed into the testing comb which is part of the tensile tester. The combing force reduction is given in percent and calculated from the force ratio between treated swatch value and blank value (untreated swatch). Each formulation was tested with 5 hair strands, using a wet and dry combing device. For the wet combing test 1 g hair strands with a length of 12 cm and for the dry combing test 2 g hair stands with a length of 15 cm were used.

The first step for the investigation of dry combability was the preparation of the hair strands for the determination of the reference values. The preparation included the equilibration of the hair strands for 12 hours at a room temperature of 23° C. and 50% relative humidity. Then the reference measurement was taken. The hair strands were treated with 0.25 g of the respective washing formulation per 1 g of hair and incubated for 5 minutes. Then the hair strands were well rinsed with tap water for about 1 minute at room temperature. This treatment with the washing formulation was repeated. The hair strands were dried, and the dried hair strands were equilibrated at the conditions given above. Then the combing measurement was performed.

The conditioning performance of the respective washing formulations was evaluated by measuring the reduction in work or energy associated with combing the hair strands. Combing force was measured by a Zwicki Z2.5 Dynamic Testing Machine (Zwick Roell, Germany) before and after treatment with the test formulation according to the description above. The percent change in combing work reduction was then calculated as the ratio of the difference between post and pre-treatment combing work to pretreatment combing work as shown below. As such, negative values indicate a reduction in combing work due to the treatment (conditioning) and positive values indicate an increase in combing work due to the treatment. The recorded force-displacement curves were integrated to calculate the combing work.

The residual combing work is calculated as following:

Residual combing work=(combing work after treatment)/(combing work before treatment) Change in combing work (%)=(Treated−Untreated)×100

Zinc Pyrithione (ZPT) Deposition Measurement

Zinc pyrithione deposition was measured by Optical Emission Spectroscopy with Inductively Coupled Plasma test (ICP-OES). A combination of each formulation (0.5 g) and water (2.5 g) was applied to a 4 cm by 4 cm VitroSkin substrate for 30 seconds to mimic normal consumer use of shampoo onto the scalp. Application was followed by rinse-off. With the VitroSkin allowed to dry naturally overnight.

The treated VitroSkin was weighed in microwave PTFE vessel and 10 mL nitric acid (65%) was added to each vessel. Microwave-assisted acid digestion (Anton Paar Multiwave Pro) was performed on the samples with the following program.

| Stage | Power (V) | Ramp (min) | Hold (min) |
|---|---|---|---|
| 1 | 350 | 10 | 0 |
| 2 | 350 | 0 | 5 |
| 3 | 700 | 10 | 0 |
| 4 | 700 | 0 | 60 |
| 5 | 0 | 0 | 30 |

The digested samples were transferred to sample tubes, diluted to a final volume of 50 mL (with deionized water) then ICP-OES (Perkin Elmer Optima 8000 DV) for analysis.

Vitro-Skin is an artificial substrate that is used in our deposition studies to mimic the surface properties of human skin. It contains both optimized protein and lipid components and is designed to have topography, pH, critical surface tension and ionic strength similar to human skin.

In the following examples all parts and percentages are by weight unless otherwise indicated.

Formulations and Results of Coacervate Weight Measurement

The personal washing formulations and the results of coacervate formation are shown in below Table 1.

TABLE 1

| Ingredients | A | A-0 | A-1 | A-2 | A-3 | A-4 | A-5 | A-6 | B | B-0 | B-1 | B-2 |
|---|---|---|---|---|---|---|---|---|---|---|---|---|
| Polyquaternium-10[1] | 0.3 | 0.3 | 0.3 | 0.3 | 0.3 | 0.3 | 0.3 | 0.3 | — | — | — | — |
| Guar Hydroxypropyltrimonium Chloride[2] | — | — | — | — | — | — | — | — | 0.3 | 0.3 | 0.3 | 0.3 |
| Cocamidopropyl betaine | 4.86 | 4.86 | 4.86 | 4.86 | 4.86 | 4.86 | 4.86 | 4.86 | 4.86 | 4.86 | 4.86 | 4.86 |
| Coco glucoside | 4.4 | 4.4 | 4.4 | 4.4 | 4.4 | 4.4 | 4.4 | 4.4 | 4.4 | 4.4 | 4.4 | 4.4 |
| Disodium Cocoyl Glutamate | 2.4 | 2.4 | 2.4 | 2.4 | 2.4 | 2.4 | 2.4 | 2.4 | 2.4 | 2.4 | 2.4 | 2.4 |
| Sodium Cocoyl Isethionate | 4 | 4 | 4 | 4 | 4 | 4 | 4 | 4 | 4 | 4 | 4 | 4 |
| Oleic acid ester of alkoxylate trimethylolpropane[3] | 0.675 | 0.675 | 0.675 | 0.675 | 0.675 | 0.675 | 0.675 | 0.675 | 0.675 | 0.675 | 0.675 | 0.675 |
| Acrylate copolymer[4] | — | 0.9 | 0.9 | 0.9 | 0.9 | 0.9 | 0.9 | 0.9 | — | 0.9 | 0.9 | 0.9 |
| Homopolymer of acrylamidomethylpropane sulfonic acid[5] | — | — | 0.1 | 0.4 | 1.0 | — | — | — | — | — | 0.3 | 0.9 |
| AMPS-AA Copolymer[6] (Molar ratio: AMPS:AA = 1:3) | — | — | — | — | — | 0.1 | — | — | — | — | — | — |
| AMPS-AA Copolymer[7] (Molar ratio: AMPS:AA = 1:1) | — | — | — | — | — | — | 0.1 | — | — | — | — | — |
| AMPS-AA Copolymer[8] (Molar ratio: AMPS:AA = 3:1) | — | — | — | — | — | — | — | 0.1 | — | — | — | — |
| Deionized water | q.s. to 100 | | | | | | | | | | | |
| Coacervate weight (g) | 1.21 | 0 | 0.45 | 0.94 | 0.76 | 0.31 | 0.45 | 0.53 | 1.3 | 0 | 0.72 | 0.57 |

[1] JR-30M, commercially available from Dow Chemical, Mw = 1,500,000-1,800,000 g/mol
[2] Jaguar Excel, commercially available from Solvay, Mw = 1,500,000 g/mol
[3] Arlypon TT, PEG/PPG-120/10 Trimethylopane Trioleate (and) Laureth-2 sold by BASF
[4] Rheocare TTA, (2-methyl-2-propenoic acid polymer with butyl 2-propenoate and ethyl 2-propenoate), commercially available from BASF.
[5] Rheocare HSP 1180, commercially available from BASF, Mw = 1,620,000 g/mol; Charge density = 4.8 meq/g
[6] Acrylic acid (AA)-acrylamidomethylpropane sulfonic acid (AMPS) copolymer was manufactured by conventional polymerization techniques well-known to one of ordinary skill in the art. Mw = 36,750 g/mol; charge density = 2.3 meq/g.
[7] Acrylic acid (AA)-acrylamidomethylpropane sulfonic acid (AMPS) copolymer was manufactured by conventional polymerization techniques well-known to one of ordinary skill in the art. Mw = 37,770 g/mol, Charge density = 3.6 meq/g.
[8] Acrylic acid (AA)-acrylamidomethylpropane sulfonic acid (AMPS) copolymer was manufactured by conventional polymerization techniques well-known to one of ordinary skill in the art. Mw = 39,360 g/mol, Charge density = 4.3 meq/g The formation of coacervates was observed in Formulations A and B, which comprise sulfate-free surfactant compositions and cationic conditioning polymer. With the addition of rheology modifying polymers to the Formulations A-0 and B-0, the coacervates were not formed. Formulations A-1, A-2, A-3, A-4, A-5, A-6, B-1 and B-2, which further comprise the additional anionic (co)polymer of polysulfonic acid, make it possible to form more coacervates.

Formulations and Results of Combing Force Measurement

The personal washing formulations and results of residual combing force are shown in Table 2.

TABLE 2

| Ingredients | C | C-0 | C-1 | C-2 | C-3 |
|---|---|---|---|---|---|
| Polyquaternium-10[1] | 0.3 | 0.3 | 0.3 | 0.3 | 0.3 |
| Cocamidopropyl betaine | 4.86 | 4.86 | 4.86 | 4.86 | 4.86 |
| Coco glucoside | 4.4 | 4.4 | 4.4 | 4.4 | 4.4 |
| Disodium Cocoyl Glutamate | 2.4 | 2.4 | 2.4 | 2.4 | 2.4 |
| Sodium Cocoyl Isethionate | 4 | 4 | 4 | 4 | 4 |
| Oleic acid ester of alkoxylate trimethylolpropane | 0.675 | 0.675 | 0.675 | 0.675 | 0.675 |
| Acrylate copolymer[2] | — | 0.9 | 0.9 | 0.9 | 0.9 |
| AA-AMPS copolymer[3] | — | — | — | 0.1 | 0.1 |
| Zinc pyrithione[4] | — | — | 0.5 | — | 0.5 |
| Deionized water | q.s. to 100 | | | | |
| Residual combing force | 18% | 74% | 66% | 56% | 43% |

[1] JR-30M, commercially available from Dow Chemical, Mw = 1,500,000-1,800,000 g/mol
[2] Rheocare TTA, commercially available from BASF.
[3] AA:AMPS = 3:1, Mw = 19,700 g/mol, charge density = 2.3 meq/g.
[4] CleanBio ™-Zinc, commercially available from Kolon.

Compared to Formulation C (which comprises cationic polymer and sulfate-free surfactant composition, but which does not include any additional rheology modifying polymer), Formulation C-0, with the addition of rheology modifying polymer, shows a higher residual combing force value, which is due to less coacervation formation and poor deposition of conditioning ingredients. Formulations C-1, C-2 and C-3, demonstrate lower residual combing force, which means improved coacervate formation and deposition of conditioning ingredients.

Formulations and Results of Zinc Deposition Measurement

The personal washing formulations and results of Zn deposition are shown in Table 3.

TABLE 3

| Ingredients | D | D-1 | D-2 | D-3 |
|---|---|---|---|---|
| Polyquaternium-10[1] | 0.3 | 0.3 | 0.3 | 0.3 |
| Cocamidopropyl betaine | 4.86 | 4.86 | 4.86 | 4.86 |
| Coco glucoside | 4.4 | 4.4 | 4.4 | 4.4 |
| Disodium Cocoyl Glutamate | 2.4 | 2.4 | 2.4 | 2.4 |
| Sodium Cocoyl Isethionate | 4 | 4 | 4 | 4 |
| Oleic acid ester of alkoxylate trimethylolpropane | 0.675 | 0.675 | 0.675 | 0.675 |
| Acrylate copolymer[2] | 0.9 | 0.9 | 0.9 | 0.9 |
| Homopolymer of acrylamidomethylpropane sulfonic acid[3] | — | 0.4 | 1.0 | |
| Acrylate homopolymer[4] | | | | 0.3 |

TABLE 3-continued

| Ingredients | Formulations (% wt (actives)) | | | |
|---|---|---|---|---|
| | D | D-1 | D-2 | D-3 |
| Zinc pyrithione[5] | 0.5 | 0.5 | 0.5 | 0.5 |
| Deionized water | | q.s. to 100 | | |
| Zn deposition (µg/cm$^2$) | 0.32 | 1.00 | 0.36 | 0.22 |

[1]JR-30M, commercially available from Dow Chemical, Mw = 1,500,000-1,800,000 g/mol
[2]Rheocare TTA, commercially available from BASF.
[3]Rheocare HSP 1180, commercially available from BASF, Mw = 1,620,000 g/mol; Charge density = 4.8 meq/g
[4]Linear polyacrylic acid, Mw = 10,300 g/mol.
[5]CleanBio ™-Zinc, commercially available from Kolon.

Compared to Formulation D (which comprises sulfate-free surfactant composition, cationic conditioning polymer, rheology modifying polymer and ZPT, which does not include the anionic (co)polymer of polysulfonic acid), Formulation D-1 and D-2, with addition of polysulfonic acid (co)polymer, demonstrate the higher amount of ZPT deposition. However, Formulation D-3, with addition of other type anionic polymer which does not contain the unsaturation monomer having sulfonic acid group, cannot bring about an enhanced ZPT deposition.

The invention claimed is:

1. A personal washing composition with enhanced deposition of benefit agents, said composition comprising:
   a) a detersive surfactant selected from the group consisting of anionic surfactants, amphoteric surfactants, zwitterionic surfactants, and combinations thereof,
   b) at least one rheology modifying polymer,
   c) at least one cationic conditioning polymer,
   d) at least one benefit agent in an effective amount to condition hair or skin,
   e) an anionic polymer of polysulfonic acid which comprises pendant sulfonate ($-SO_3^-$) and/or pendant sulfonic acid group ($-SO_3H$),
   f) a cosmetically acceptable carrier;
   wherein the personal washing composition is sulfate-free or substantially sulfate-free, and
   wherein the benefit agent is an anti-dandruff agent, and the benefit agent is small particles dispersed in the composition, the benefit agent having an average particle diameter in a range of from 0.01 µm to 400 µm.

2. The composition according to claim 1, wherein the anionic polymer of polysulfonic acid comprises at least one monomer having ethylenic unsaturation with a sulfonic group, which is selected from the group consisting of 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propene-1-sulfonic acid, styrenesulfonic acid, vinylsulfonic acid, 3-sulfopropyl acrylate, 3-sulfopropyl methacrylate, sulfomethacrylamide, sulfomethylmethacrylamide, and mixtures of the stated acids or the water-soluble salts thereof.

3. The composition according to claim 1, wherein the anionic polymer of polysulfonic acid is selected from the group consisting of homopolymer of acrylamido-2-methylpropanesulfonate, copolymer of acrylamido-2-methylpropanesulfonate, and a combination thereof.

4. The composition according to claim 1, wherein the anionic polymer of polysulfonic acid optionally comprises a comonomer containing a carboxylic acid group which is selected from the group consisting of acrylic acid, methacrylic acid, ethacrylic acid, a-chloroacrylic acid, a-cyanoacrylic acid, crotonic acid, a-phenylacrylic acid, maleic acid, maleic anhydride, fumaric acid, itaconic acid, citraconic acid, methylenemalonic acid, sorbic acid, cinnamic acid, and mixtures thereof.

5. The composition according to claim 1, wherein said anionic polymers of polysulfonic acid has a charge density in the range of from 0.1 meq/g to 9.5 meq/g.

6. The composition according to claim 1, wherein the benefit agent has an average particle diameter in the range of from 0.01 µm to 200 µm.

7. The composition according to claim 1, wherein the anionic surfactant comprises a compound selected from the group consisting of a sulfonate, a sulfosuccinate, a carboxylate, a sarcosinate, an isethionate, a sulfoacetate, and combinations thereof.

8. The composition according to claim 1, wherein the at least one rheology modifying polymer is an associative rheology modifying polymer selected from the group consisting of hydrophobically modified alkali-swellable and alkali-soluble emulsion polymers.

9. The composition according to claim 1, wherein the cationic conditioning polymer is selected from the group consisting of cationic polysaccharides and polymers comprising cationic vinyl monomers.

10. The composition according to claim 1, wherein the anionic polymer of polysulfonic acid is present in an amount ranging from 0.01 wt % to 10 wt %.

11. The composition according to claim 1, wherein the composition is a cosmetic hair composition applied to the hair for washing, conditioning, or styling purposes.

12. The composition according to claim 1, wherein the composition is a hair shampoo, a hair conditioner, a hair treatment, or a hair styling composition.

13. A method of achieving improved conditioning benefits, comprising applying to skin and/or hair the composition according to claim 1.

14. A method of achieving improved deposition of benefit agents onto hair and/or skin, comprising applying to hair and/or skin the composition according claim 1.

15. A method of achieving improved deposition of benefit agents onto hair and/or skin according to claim 14, wherein the benefit agent is dispersed in the composition and has a small particle size.

16. The composition according to claim 1, wherein the cationic conditioning agent is selected from the group consisting of cationic guar gum derivatives, cationic cellulose derivatives, cationic starch derivatives, homopolymers and copolymers of dimethyl diallyl ammonium chloride (DM-DAAC), homopolymers and copolymers of methacrylamidopropyl trimethyl ammonium chloride (MAPTAC), homopolymers and copolymers of acrylamidopropyl trimethyl ammonium chloride (APTAC), homopolymers and copolymers of methacryloyloxyethyl trimethyl ammonium chloride (METAC), homopolymers and copolymers of acryloyloxyethyl trimethyl ammonium chloride (AETAC), homopolymers, copolymers of methacryloyloxyethyl trimethyl ammonium methyl sulfate (METAMS) and a combination thereof.

17. The composition according to claim 8 wherein the associative rheology modifying polymer comprises copolymers of hydrophilic methacrylates or acrylates and of hydrophobic monomers comprising at least one fatty chain; copolymer of vinylpyrrolidone and of fatty-chain hydrophobic monomers; hydrophobically modified ethylene oxide urethane polymers; hydrophobically modified hydroxyethyl cellulose polymers, hydrophobically modified hydroxypropyl guar polymers, and mixtures thereof.

18. The composition according to claim 1 wherein the benefit agent has an average diameter in the range of 0.01 µm to 100 µm.

19. The composition according to claim 1 wherein the benefit agent has an average diameter in the range of 0.01 µm to 50 µm.

\* \* \* \* \*